United States Patent
Marxer et al.

(10) Patent No.: US 7,477,371 B2
(45) Date of Patent: *Jan. 13, 2009

(54) PROCESS AND ASSEMBLY FOR NON-DESTRUCTIVE SURFACE INSPECTIONS

(75) Inventors: Norbert Marxer, Schaanwald (LI); Kenneth P. Gross, San Carlos, CA (US); Hubert Altendorfer, Redwood Shores, CA (US); George Kren, Los Altos, CA (US)

(73) Assignee: KLA-Tencor Corporation, Milpitas, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 11/464,766

(22) Filed: Aug. 15, 2006
(Under 37 CFR 1.47)

(65) Prior Publication Data

US 2007/0103676 A1    May 10, 2007

Related U.S. Application Data

(60) Division of application No. 10/619,109, filed on Jul. 10, 2003, now Pat. No. 7,102,744, which is a continuation of application No. 09/901,998, filed on Jul. 10, 2001, now Pat. No. 6,606,153, which is a continuation of application No. 08/770,491, filed on Dec. 20, 1996, now Pat. No. 6,271,916, which is a continuation-in-part of application No. 08/533,632, filed on Sep. 25, 1995, now abandoned, and a continuation-in-part of application No. 08/216,834, filed on Mar. 24, 2004, now abandoned.

(51) Int. Cl.
*G01N 21/00* (2006.01)

(52) U.S. Cl. ............................ 356/237.2; 356/237.1
(58) Field of Classification Search .... 356/237.2–237.5
See application file for complete search history.

(56) References Cited

U.S. PATENT DOCUMENTS 4,314,763 A * 2/1982 Steigmeier et al. ....... 356/237.2
4,360,275 A   11/1982 Louderbeck
4,378,159 A    3/1983 Galbraith (Continued)

FOREIGN PATENT DOCUMENTS

| DE | 250850 | 10/1987 |
|---|---|---|
| DE | 4123916 | 1/1992 |
| DE | 4134747 A1 | 4/1993 |

(Continued)

OTHER PUBLICATIONS

Figure, Hitachi Electronics Engineering Co., Ltd., presented by Etsuro Morita of Mitsubishi Materials Silicon Corp. in a presentation entitled "Exploration of COP and COP Defect Crystal Originated 'Particles'." at the 6th International Workshop on 300 Millimeter Wafers on Dec. 5, 1996 in Makuhari. Japan.

(Continued)

*Primary Examiner*—L. G. Lauchman
*Assistant Examiner*—Jarreas C Underwood
(74) *Attorney, Agent, or Firm*—Davis Wright Tremaine LLP

(57) ABSTRACT

A light beam is directed towards a surface along a direction normal to the surface. The surface is caused to move so that the beam scans the surface along a spiral path. An ellipsoidal mirror is placed with its axis along the surface normal to collect light scattered by the surface and any anomalies at the surface at collection angles away from the surface normal. In some applications, a lens arrangement with its axis along the surface normal is also used to collect the light scattered by the surface and any anomalies. The light scattered by the mirror and lenses may be directed to the same or different detectors. Preferably light scattered by the surface within a first range of collection angles from the axis is detected by a first detector and light scattered by the surface within a second range of collection angles from the axis is detected by a second detector. The two ranges of collection angles are different, with one detector optimized to detect scattering from large particles and defects and the other detector optimized to detect light from small particles and defects.

48 Claims, 11 Drawing Sheets

U.S. PATENT DOCUMENTS

| | | | |
|---|---|---|---|
| 4,391,524 A | | 7/1983 | Steigmeier et al. |
| 4,395,126 A | | 7/1983 | Kramer |
| 4,423,331 A | | 12/1983 | Koizumi et al. |
| 4,449,818 A | | 5/1984 | Yamaguchi et al. |
| 4,479,714 A | | 10/1984 | Lehrer |
| 4,508,450 A | * | 4/1985 | Ohshima et al. ......... 356/237.2 |
| 4,523,841 A | | 6/1985 | Brunsting et al. |
| 4,526,468 A | | 7/1985 | Steigmeier et al. |
| 4,540,286 A | | 9/1985 | Satake et al. |
| 4,558,949 A | | 12/1985 | Uehara et al. |
| 4,589,773 A | | 5/1986 | Ido et al. |
| 4,598,997 A | | 7/1986 | Steigmeier et al. |
| 4,669,875 A | | 6/1987 | Shiba et al. |
| 4,735,504 A | | 4/1988 | Tycko |
| 4,740,079 A | | 4/1988 | Koizume et al. |
| 4,744,663 A | | 5/1988 | Hamashima et al. |
| 4,794,264 A | | 12/1988 | Quackenbos et al. |
| 4,794,265 A | * | 12/1988 | Quackenbos et al. ... 250/559.45 |
| 4,861,164 A | | 8/1989 | West |
| 4,893,032 A | | 1/1990 | Braden |
| 4,893,932 A | | 1/1990 | Knollenberg |
| 4,898,471 A | | 2/1990 | Stonestrom et al. |
| 4,929,845 A | | 5/1990 | Amir et al. |
| 4,957,368 A | * | 9/1990 | Smith ......................... 356/369 |
| 4,966,457 A | * | 10/1990 | Hayano et al. ........... 356/239.7 |
| 5,058,982 A | | 10/1991 | Katzir |
| 5,076,692 A | | 12/1991 | Neukermans et al. |
| 5,108,176 A | * | 4/1992 | Malin et al. ............... 356/243.1 |
| RE33,956 E | | 6/1992 | Lin et al. |
| 5,125,741 A | * | 6/1992 | Okada et al. ............. 356/237.2 |
| 5,155,372 A | | 10/1992 | Bowen et al. |
| 5,189,481 A | | 2/1993 | Jann et al. |
| 5,245,403 A | * | 9/1993 | Kato et al. ................ 356/239.8 |
| 5,270,794 A | | 12/1993 | Tsuji et al. |
| 5,315,609 A | | 5/1994 | Tanaka et al. |
| 5,377,001 A | | 12/1994 | Malin et al. |
| 5,377,002 A | | 12/1994 | Malin et al. |
| 5,389,794 A | | 2/1995 | Allen et al. |
| 5,406,367 A | | 4/1995 | Sopori |
| 5,416,594 A | | 5/1995 | Gross et al. |
| 5,424,838 A | | 6/1995 | Siu |
| 5,463,459 A | | 10/1995 | Morioka et al. |
| 5,465,145 A | | 11/1995 | Nakashige et al. |
| 5,486,919 A | | 1/1996 | Tsuji et al. |
| 5,530,550 A | | 6/1996 | Nikoonahad et al. |
| 5,585,916 A | * | 12/1996 | Miura et al. .............. 356/237.4 |
| 5,608,526 A | | 3/1997 | Piwonka-Corle et al. |
| 5,650,614 A | | 7/1997 | Yasutake et al. |
| 5,672,885 A | | 9/1997 | Allen et al. |
| 5,712,701 A | | 1/1998 | Clementi et al. |
| 5,798,829 A | | 8/1998 | Vaez-Iravani |
| 5,888,710 A | | 3/1999 | Adachi et al. |
| 5,903,342 A | | 5/1999 | Yatsugake et al. |
| 5,929,983 A | | 7/1999 | Lu |
| 5,940,175 A | | 8/1999 | Sun |
| 6,081,325 A | | 6/2000 | Leslie et al. |
| 6,084,664 A | | 7/2000 | Matsumoto et al. |
| 6,104,481 A | * | 8/2000 | Sekine et al. ............. 356/237.5 |
| 6,118,525 A | | 9/2000 | Fossey et al. |
| 6,169,601 B1 | | 1/2001 | Eremin et al. |
| 6,178,257 B1 | | 1/2001 | Alumot et al. |
| 6,201,601 B1 | | 3/2001 | Vaez-Iravani et al. |
| 6,271,916 B1 | | 8/2001 | Marxer et al. |
| 6,292,259 B1 | | 9/2001 | Fossey et al. |
| 6,384,910 B2 | | 5/2002 | Vaez-Iravani et al. |
| 6,538,730 B2 | | 3/2003 | Vaez-Iravani et al. |
| 6,606,153 B2 | | 8/2003 | Marxer et al. |
| 6,618,134 B2 | | 9/2003 | Vaez-Iravani et al. |
| 6,639,662 B2 | | 10/2003 | Vaez-Iravani et al. |
| 6,657,714 B2 | | 12/2003 | Almogy et al. |
| 6,657,715 B2 | | 12/2003 | Vaez-Iravani et al. |
| 6,768,543 B1 | * | 7/2004 | Aiyer ....................... 356/237.4 |
| 6,862,096 B2 | | 3/2005 | Vaez-Iravani et al. |
| 6,891,611 B1 | | 5/2005 | Vaez-Iravani et al. |
| 6,922,236 B2 | | 7/2005 | Vaez-Iravani et al. |
| 6,956,644 B2 | | 10/2005 | Biellak et al. |
| 7,102,744 B2 | | 9/2006 | Marxer et al. |
| 7,119,897 B2 | | 10/2006 | Vaez-Iravani et al. |
| 2004/0057045 A1 | | 3/2004 | Vaez-Iravani et al. |
| 2005/0134841 A1 | | 6/2005 | Vaez-Iravani et al. |

FOREIGN PATENT DOCUMENTS

| | | |
|---|---|---|
| EP | 0 290 228 | 11/1988 |
| EP | 0 624 787 | 11/1994 |
| EP | 0 715 147 A2 | 6/1996 |
| JP | 57-13340 | 1/1982 |
| JP | 6-14830 | 1/1988 |
| JP | 63-140904 A | 6/1988 |
| JP | 63-284455 A | 11/1988 |
| JP | 63-285449 | 11/1988 |
| JP | 5-332946 | 12/1993 |
| JP | 63-14830 A | 11/1994 |
| WO | WO 96/15354 | 0/1996 |
| WO | WO 97/04134 | 3/1997 |
| WO | WO 97/12226 | 4/1997 |
| WO | WO 97/33158 | 9/1997 |
| WO | WO 99/14575 | 3/1999 |

OTHER PUBLICATIONS

Yatsugake et al., "Surface Inspection System for Estimation of Wafer," *Hitachi Electronics Engineering Technical Report*, vol. 11, Jan. 1996, pp. 21-26.

"Integrating Sphere Theory," Laser Beam Measurement, Melles Griot, The Practical Application Of Light, 1999-2004, pp. 1-5.

"Integrating Sphere," Melles Griot , Glossary, The Practical Application Of Light, 2000-2004, pp. 1.

"Bespoke Integrating Spheres now off-the-shelf," Laboratorytalk, Product news, Pro-Lite Technology, May 14, 2004, pp. 1-2.

"Integrating Sphere Fabrication and Coating," Applications, Labsphere, pp. 1.

"A Guide to Reflectance Coatings and Materials," Techguide, Labsphere, pp. 1-8.

"Integrating Spheres," Spectral Products, 2003, pp. 1-2.

Fujise et al., "Determination of COP distribution after SCI cleaning by a laser particle counter," Optical Characterization Techniques for High-Performance Microelectronic Device Manufacturing III, SPIE vol. 2877, pp. 16-25.

Eremin et al., "Discrete Sources Method for the Silicon Wafers Defect Discrimination," 12th Annual Review of Progress in Applied Computational Electromagentics, Mar. 18-22, 1996, pp. 758-762.

Wagner et al, "Requirements for Future Surface Inspection Equipment for Bare Silicon Surfaces," Wacker-Chemitronic GmbH, Burghausen, Germany, W. Baylies, BayTech Group, Weston Massechussets, 8 pages.

Knollenberg et al., "The Importance of Media Refractive Index in Evaluating Liquid and Surface Microcontamination Measurements," The Journal of Environmental Sciences, Mar./Apr. 1987, 9 pages.

International Search Report Issued by the International Patent Office (WIPO) corresponding to the International Patent Application No.: PCT/US96/15354 issued on Dec. 27, 1996, 1 page.

Notification of Transmittal of International Preliminary Examination Report, dated Nov. 19, 1997, issued in corresponding PCT Appln. No. PCT/US96/15354, 12 pages.

Written Opinion issued Jul. 15, 1997 in corresponding PCT Appln. No. PCT/US96/15354, 3 pages.

* cited by examiner

PROCESS AND ASSEMBLY FOR NON-DESTRUCTIVE SURFACE INSPECTIONS

CROSS-REFERENCE TO RELATED APPLICATIONS

This application is a divisional of application Ser. No. 10/619,109, filed Jul. 10, 2003; which application is a continuation of application Ser. No. 09/901,998, filed Jul. 10, 2001, now U.S. Pat. No. 6,606,153; which application is a continuation of application Ser. No. 08/770,491, filed Dec. 20, 1996, now U.S. Pat. No. 6,271,916; which application is a continuation-in-part of application Ser. No. 08/533,632, filed Sep. 25, 1995, now abandoned; and also a continuation-in-part of application Ser. No. 08/216,834, filed Mar. 24, 2004, now abandoned. These applications are incorporated by reference in their entirety as if fully set forth herein.

BACKGROUND OF THE INVENTION

The invention described in the present disclosure relates to a process and an assembly for the non-destructive inspection of surfaces, particularly for the measurement of small particles, defects, and inhomogeneities on and/or just below the surface of a test object, such particles, defects, and inhomogeneities collectively referred to herein as anomalies. It relates in particular to an instrument described below as the preferred embodiment for inspecting a silicon wafer, the instrument having a light source that generates a light beam, a beam deflector, an optical system that projects the incident beam on a light spot perpendicular to the test object, a photodetector to which the collected light is guided, and an assembly by which the test object is moved by a coordinated translational and rotary movement, so that the light spot scans the whole of the surface along a spiral path.

Such types of process and/or assembly can be used, for example in microelectronics, for the non-destructive checking and inspection of the surfaces of wafers, magnetic storage media, and/or substrates for optical applications, to determine the presence of any particles and/or defects.

The development of wafer-exposure processes has made it possible to manufacture wafer surfaces with ever finer structures parallel to this development, inspection systems that permit the detection of ever more minute defects and particles have become increasingly important. Apart from particles that account for about 75% of all waste in the manufacture of integrated circuits (ICS), inspection systems must be capable of detecting many other types of inhomogeneity, such as variations in the thickness of coatings, crystal defects on and below the surface, etc.

In the final inspection by wafer manufacturers and the inward-goods inspection by chip manufacturers, the unstructured, uncoated wafer must therefore be subjected to extremely searching examination for particle contamination, light-point crystal defects, roughness, polishing scratches, etc. If the test object has a rough surface, then a large amount of stray surface scattering will result. Thus, for this purpose, the test object has a well-polished surface that produces very little diffused light.

In chip manufacture it is usual to monitor each stage of the process, in order to recognize problems as early as possible and thus avoid undue waste. One method of process monitoring is to use so-called monitor wafers which remain unstructured but pass through some of the process stages. Comparison of two measurements, the first before the process stage and the other after it, can thus, for example, help determine the amount of particle contamination due to that process stage or indicate variations in the evenness of the process stage, for example the distribution of the coating thickness over the whole of the wafer. The surfaces subjected to inspection may be rough and metallized, and therefore, produce a great deal of diffused light, or they may be film-coated surfaces that cause interference-fringe effects. Thus, ideally the inspecting instrument has a wide dynamic range to permit defect and particle detection of a wide variety of surfaces.

PRIOR ART

For the type of inspection described above, so-called laser scanners are particularly suitable. An important feature of these is their high sensitivity to very small defects and the ability to determine the presence of these, and their high throughput. The main differences in the laser scanners now available are the type of scanning they use, their optical configuration, and the manner in which the results are processed.

For applications that require a high throughput and 100% inspection of the whole wafer surface, two processes are mainly used. In the first of these, for example as described in U.S. Pat. No. 4,314,763, the illuminating beam and the collecting optics are stationary, and the test object is scanned spirally by means of a coordinated translational and rotary movement of the test object itself. In the second process, for example as described in U.S. Pat. No. 4,378,159, a rotating or vibrating mirror moves the illuminating beam in one direction linearly back and forth across the wafer, and the whole of the wafer is scanned by virtue of a simultaneous translational movement of the test object perpendicular thereto.

Spiral scanning has the following advantages:
the optical system has no moving parts and thus is simpler;
the illuminated spot and the collector system's field remain constant during the whole of the measurement procedure, hence the system's sensitivity is homogeneous over the whole of the test object;
the system takes up less room, because the test object has to be moved only by the length of its radius; and
there is no need to alter the optical system for inspection of bigger objects, only the travel of the translational stage.

The advantages of moving the illuminating beam by means of a mirror or a set of mirrors are:
the test object has to be moved in one direction only, and this is simpler; and
as a rule, scanning is faster.

In the second scanning method, because the illuminating spot moves across the test object and thus the source of diffused light moves in relation to the optical collector system, it cannot ensure an even measuring sensitivity, nor does it permit a rotationally symmetrical arrangement of the collector optics. These are serious drawbacks in laser scanners configured in this manner.

Various optical configurations are known from prior art in the use of a laser scanner for spiral scanning as described above.

For example, U.S. Pat. No. 4,893,932 describes a system which has two differently polarized lasers and two corresponding detectors. The diffused-light intensity of spheres as a function of their diameter has oscillations for diameters within the range of the wavelength used and increases strictly monotonically for smaller diameters. The use of differently polarized light reduces the error in the attribution of diffused-light intensity to particle diameter for the spheres of polystyrene latex (PSL) spheres used for the calibration of laser scanners.

But in practice, the attribution of certain diffused-light intensities to particle diameters depends on so many factors, such as substrate material, films and coatings available, particle material, surface texture of particles, etc., that when the optics and calibration of the equipment are designed only for polystyrene-latex spheres, they tend to make interpretation of the results more difficult. A further major drawback of this method is that the oblique angle of incidence and linear polarization of the laser beam break the symmetry. The measured signal thus depends on the orientation of the defect.

Japanese Patent Application No. 6-314830 describes collector optics made up of concentric rings, each having six fibre-optic light guides, which are directed to a photomultiplier. The drawbacks of this arrangement are that it fails to cover the central zone near the axis, and the discrete arrangement can achieve rotational symmetry only approximately.

EP-A-0290228 describes an arrangement whereby the diffused light is conducted to two detectors. The first detector collects light deflected by about 40 mrad to 100 mrad, the second collects light diffused by more than 100 mrad. Such an angle-resolving method of measurement by means of two detectors makes it possible to classify the defects, but because the collector angle is limited, the system cannot measure very small defects.

DE-A4,134,747 describes a similar solution that uses two detectors designed as arrays, one of which measures the radial and the other the azimuthal light distribution. In this system the test object rotates and the optical system moves linearly.

DD 250,850 also describes an angle-resolving method of measuring diffused light by means of fiber-optic light guides arranged in a circle.

Both the above methods have the drawback that the collector angle is much smaller and closer to specular than that described in the present disclosure.

In this connection, U.S. Pat. No. 4,314,763 describes a design in which perpendicular incident light and rotational symmetry of the collector optics about the perpendicular of the test object permit measurements regardless of the defect's orientation. But the lens system used only has a small collector angle and this limits the capability of the design in detection of very small particles at a high throughput rate.

The same inventor's U.S. Pat. No. 4,598,997 improves the measurement of textured or structured surfaces by the addition of a special mask to the design described above. The purpose of the mask is to suppress the rays deflected by these structures.

A significant drawback of prior art systems is the inability to detect very small surface or near surface defects and particles. With the continual reduction in size of semiconductor structures on wafer surfaces, it is critically important to be able to detect such small anomalies. As shown in Table 34 of The National Technology Roadmap for Semiconductors by The Semiconductor Industry Association, 1994, the requirements for defect and particle detection sensitivity will be 0.08 micron in 1998, 0.05 or 0.06 micron in 2001 and down to 0.02 micron in 2010. None of the above referenced systems is capable of achieving sensitivities that are close to such requirements.

SUMMARY OF THE INVENTION

As noted above, it is difficult for prior art systems to detect small anomalies such as small particles and defects. Small particles or defects scatter light at large angles to the normal direction of the surface when the surface is illuminated in the normal direction. In normal illumination prior art systems where the light scattered by the surface is collected by a lens system where the axis of the lens system is along the normal direction, the lens system will collect only a small portion of the light scattered by such small anomalies. If large anomalies such as particles or surface defects are also present in addition to the small anomalies, the scattering from such large anomalies will be at much higher intensities compared to and will mask those caused by the small anomalies so that the small anomalies become difficult or impossible to detect. One aspect of the invention is based on the recognition that, since the scattering from the large anomalies is at much higher intensities at specular or near specular collection angles (that is, small angles to the normal) than at large collection angles whereas the scattering from small anomalies have intensities which are more evenly distributed in all directions to the normal, with most of the energy contained in the larger angles. The detection of the small anomalies can therefore be much enhanced by using an ellipsoidal mirrored surface to collect light scattered at relatively large collection angles to the normal and avoiding light scattered at specular or near specular directions.

Thus, one aspect of the invention is directed towards an optical system for detecting contaminates and defects on a test surface comprising a source of light to produce a beam, means for directing the beam along a path onto the test surface, producing an illuminated spot thereon. The system further includes an ellipsoidal mirrored surface having an axis of symmetry substantially coaxial with the path, defining an input aperture positioned proximate to the test surface to receive scattered light therethrough from the surface. The mirrored surface reflects and focuses light that is rotationally symmetric about said axis of symmetry and that passes through the input aperture at an area. The system further includes means for detecting light focused to the area.

When it is known that the surface scattering or haze level is low, and that there are few large defects or point-anomalies, detection sensitivity for small anomalies can be further enhanced by adding to the ellipsoidal mirrored surface of the above apparatus a lens assembly that collects light scattered in a small angle region near the specular direction and focuses the collected light to the same area as the ellipsoidal mirrored surface.

Another aspect of the invention is based on the observation that larger particles scatter light at smaller angles to the normal direction of the surface (i.e. direction of the specularly reflected beam) compared to smaller particles, and the light scattered by the smaller particles is lower in intensity compared to the light scattered by larger particles or defects. Where light scattered in a range of angles covering the collection angles for both large and small particles is collected and directed to a single detector means, and if the detector means is optimized for detecting the low intensity light scattered by smaller particles, the detector means may become saturated by the high intensity light scattered by larger particles. On the other hand, if the detector means is optimized for detecting the high intensity light scattered by larger particles, it is not optimized to detect low intensity light scattered by the smaller particles.

Furthermore, the surface texture itself produces a certain amount of diffracted light in addition to the light scattered by particles. This surface light scatter, commonly referred to as haze, tends to be concentrated at smaller angles near the specularly reflected light beam. If a single detector arrangement is used to detect scattered light from both large and small particles or defects, the effect of haze is to significantly degrade the signal-to-noise ratio for the detection of the smaller defects and particles.

This aspect of the invention is based on the observation that, by collecting scattered light in directions close to and at smaller angles to the specular reflection direction separately from light scattered at larger angles to the specular reflection direction and directing the light scattered at smaller angles to a different detector than the light scattered at larger angles, it is now possible to optimize the two or more detectors separately. Thus, two or more detectors are used: at least a first detector for detecting the low intensity light scattered by smaller particles at larger angles to the specular reflection direction, and at least a second detector for detecting the high intensity light scattered by larger particles at smaller angles to the specular reflection direction. The first detector will not be seriously affected by scattering due to haze, since such scattering decreases rapidly at larger angles from the specular reflection direction.

The above concept is applicable even where the light beam for illuminating the surface to be inspected is at an oblique angle to the surface instead of being perpendicular to the surface and is also applicable for the differentiation, characterization and/or classification of different types of surface or near surface anomalies (referred to below simply as anomalies of surfaces or surface anomalies), including but not limited to anomalies such as scratches, slip lines, crystal originated particles (COPs) as well as contamination particles.

As indicated above, the requirements for detection sensitivity are becoming more and more stringent. For such purpose, it is desirable to focus the illuminating beam onto a small spot on the inspected surface, such as one no larger than 50 microns in dimensions in any direction on the surface. This will enhance signal-to-noise ratio.

Thus, another aspect of the invention is directed towards an apparatus for detecting anomalies of surfaces, comprising means for focusing a light beam along a path towards a spot on a surface, causing a specular reflection, said spot having dimensions less than 50 microns; means for causing rotational and translational movement of the surface, so that the beam scans the surface along a spiral path. The apparatus further comprises a first detector located to detect light scattered by the surface within a first range of collection angles and a second detector located to detect light scattered by the surface within a second range of collection angles, said second range being different from the first range; and an ellipsoidal mirrored surface defining an input aperture positioned approximate to the surface to receive scattered light therethrough from the surface, the mirrored surface reflecting and focusing light passing through the input aperture at the first detector; and a lens assembly collecting light passing through the input aperture, defining collected light, said lens assembly focusing the collected light to the second detector.

Yet another aspect of the invention is based on the observation that if the lens used for collecting light to a detector is also used to focus the illuminating beam towards the surface inspected, stray reflections and scatter of the illuminating beam at the collection lens can cause such background light to be detected by the detector. This introduces errors and is undesirable. Thus, another aspect of the invention is directed towards an apparatus for detecting anomalies of surfaces, comprising means for directing a light beam towards a surface in a direction substantially normal to the surface, said direction defining an axis; means for causing relative motion between the surface and the beam, so that the beam scans the surface; and means for detecting light scattered by said surface. The detecting means includes at least one lens for collecting light to be detected, wherein the directing means directs light towards the surface along an illumination path that does not pass through said at least one lens. The detecting beam preferably includes at least two detectors: a first detector located to detect light scattered by the surface within the first range of collection angles from the axis and a second detector located to detect light scattered by the surface within a second range of collection angles from the axis, said second range being different from the first range.

BRIEF DESCRIPTION OF THE DRAWINGS

For simplicity in description, identical components are identified by the same numerals.

DETAILED DESCRIPTION OF THE PREFERRED EMBODIMENTS

Figure 1:
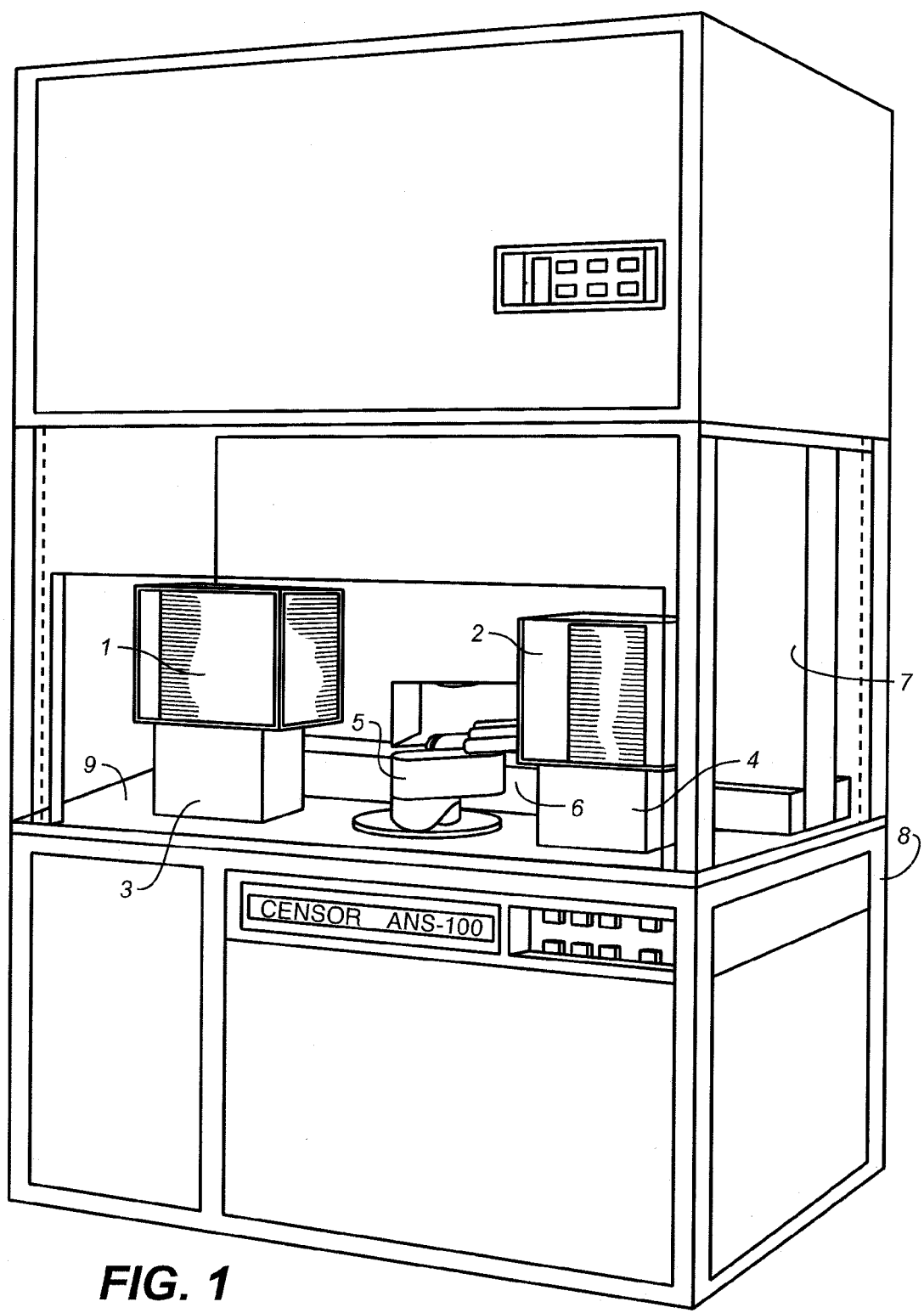
FIG. 1 is a perspective view of a wafer-inspection assembly, with two wafer cassettes and an automatic wafer-transport and wafer-measuring device.

The purpose of the present invention is, therefore, to propose a method and an assembly that avoids the drawbacks of prior art as described above and whose measuring sensitivity for particles and defects on test objects subjected to inspection is substantially greater, but without limiting haze sensitivity. At the same time, it should provide simple means to permit the adjustment of the sensitivity of the assembly, the size of the illuminated spot on the test object, and thus of the amount of diffused light generated by point defects. In addition, it should make available as large an unmodified portion of the diffused light as possible, to provide a flexible means of selectively separating and further processing the relevant parts of the diffused light, to suit the particular inspection task at hand.

The present disclosure achieves these aims by the characteristic features described below which provide the main advantages of the invention, namely:

the spatially stationary arrangement of projection and collector optics ensures that when the test object is moved parallel to its surface the measuring sensitivity remains constant over the whole surface of the object;

because the incident beam and collector optics are rotationally symmetrical about a line perpendicular to the test object's surface, the orientation of a defect such as polishing scratch does not affect measuring sensitivity;

use of a rotationally symmetrical ellipsoidal mirror creates a very large area for the collection of diffused light, and this is very important for the detection of particles in the 100 nm range and below, that diffuse fairly evenly throughout the hemisphere;

an appropriate lens system that allows light collection in the central zones near the axis is particularly important for the detection of particles in the 1 μm and above range, because of the extensive amount of scattering of such particles at smaller angles to the normal direction of the surface; and projection on a collection diaphragm of the image of the light diffused by the illuminated spot provides great design for a large variety of aperture configurations and makes possible positionally resolved, angle resolved, polarizing, and other measurements, without thereby affecting the illuminating beam or requiring any adjustments to the central part of the assembly, comprised of an ellipsoidal mirror, a lens system, a beam deflector, and a dark field stop. This is crucially important in view of the fact that the specified quality of these components is very high and precise dimensioning is extremely delicate. For example, the haze level for top-quality wafers is about 50 ppb (parts per billion), hence only about 0.000,000,05 of the total amount of light introduced is directed to the photosensor. Because haze interferes with the measurement of the smallest particles, it is essential to keep it to a minimum. To prevent measurements being affected (impaired), this also means that parasitic and ambient light from optical components must be much less than 50 ppb.

The assembly can be further improved by the use of different lens combinations in the projection optics to project the image of the illuminated spot to suit the test object, thus providing greater flexibility as to the size and shape of the illuminated spot. This also makes it possible to adjust the measuring sensitivity to different types and shapes of particles and surface defects that depend on the illuminating spot profile.

In a useful further development of the invention described in the present disclosure by a different configuration of the collection diaphragm or of the light guides above the collection diaphragm:

the signal-to-noise ratio can be improved for particle measurement by the selective adjustment of the optimum collection angle;

defects with certain diffusion properties can be either selected or suppressed;

angle-resolved diffused-light measurement for the known light-reflection behavior of different types of defects can be used for defect classification; and certain spatial frequencies of the surface can be separated.

In yet another configuration, variable attenuators are fitted above the collection diaphragm to permit the photodetector to operate in its optimum working range. In other words, where the reflection or scattering from the surface is at high intensity, such as where the surface is metallized, the attenuator will reduce the intensity to a value within the detector optimum working range. Where the reflection or scattering from the surface is not at high intensity, attenuation applied by the attenuator may be reduced or disabled so that the intensity detected is at a value within the detector optimum working range. This increases the dynamic range of the detector for detecting a wide range of intensities from a wide variety of surfaces. These are a simple means for reducing the amount of light, but do not affect the projection or collector beam.

FIG. 1 shows a substrate-surface inspection system as used mainly for the inspection of wafers. Such systems are used to display the presence of extremely small particles (i.e. about 100 nm in size), crystal defects, metallic impurities, polishing defects, scratches, and of implant and other inhomogeneities on wafers.

One condition for the measurement of very small particles in the 80 nm range is that it must be performed in a very clean environment, such as a class 1 clean room.

A state-of-the-art means of ensuring the requisite cleanliness for such measurements is, for example, the use of a flow box and an aerodynamically transparent design.

Figure 2:
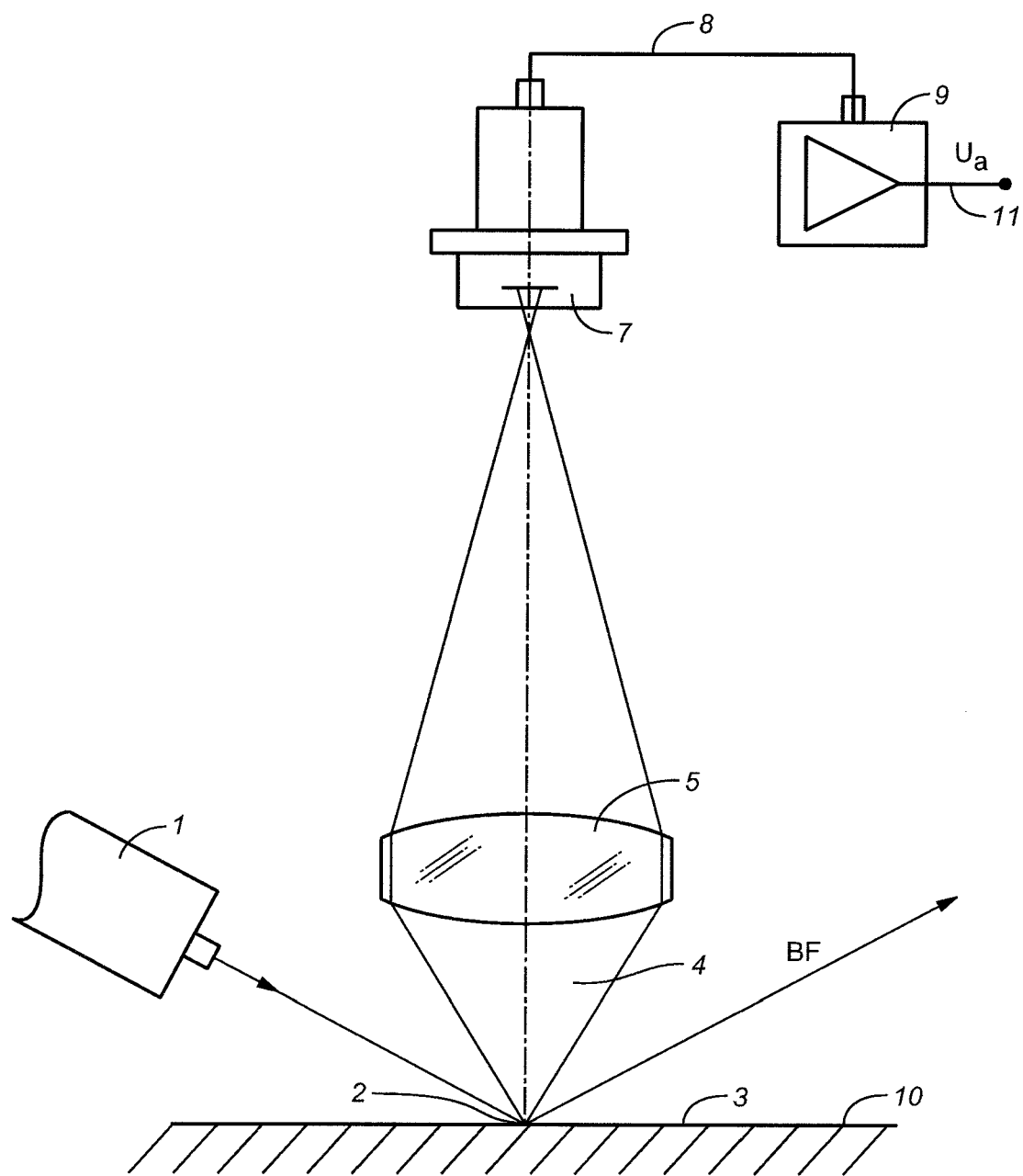
FIG. 2 is a diagrammatic representation of the present state of the art.

FIG. 2 is a diagrammatic representation of a state-of-the-art surface inspection system based on the principle of measuring elastic diffusion. A light source 1, usually a laser beam, illuminates a dot-shaped point 2 on the surface of a wafer 3. The specular reflected light leaves the system in the direction of arrow BF. A first lens 5 collects part 4 of the light diffused by the surface and projects its image to a photodetector 7. An output signal 8 from the photodetector 7 is conducted to an amplifier 9. The wafer surface 3 subjected to inspection lies in the so-called focal plane 10. If there is a defect at the illuminated position 2, the amount of diffused light 4 increases, as does the intensity of the light reaching the photodetector 7, and hence the output voltage ($U_a$) 11 from the amplifier 9 also rises.

Figure 3:
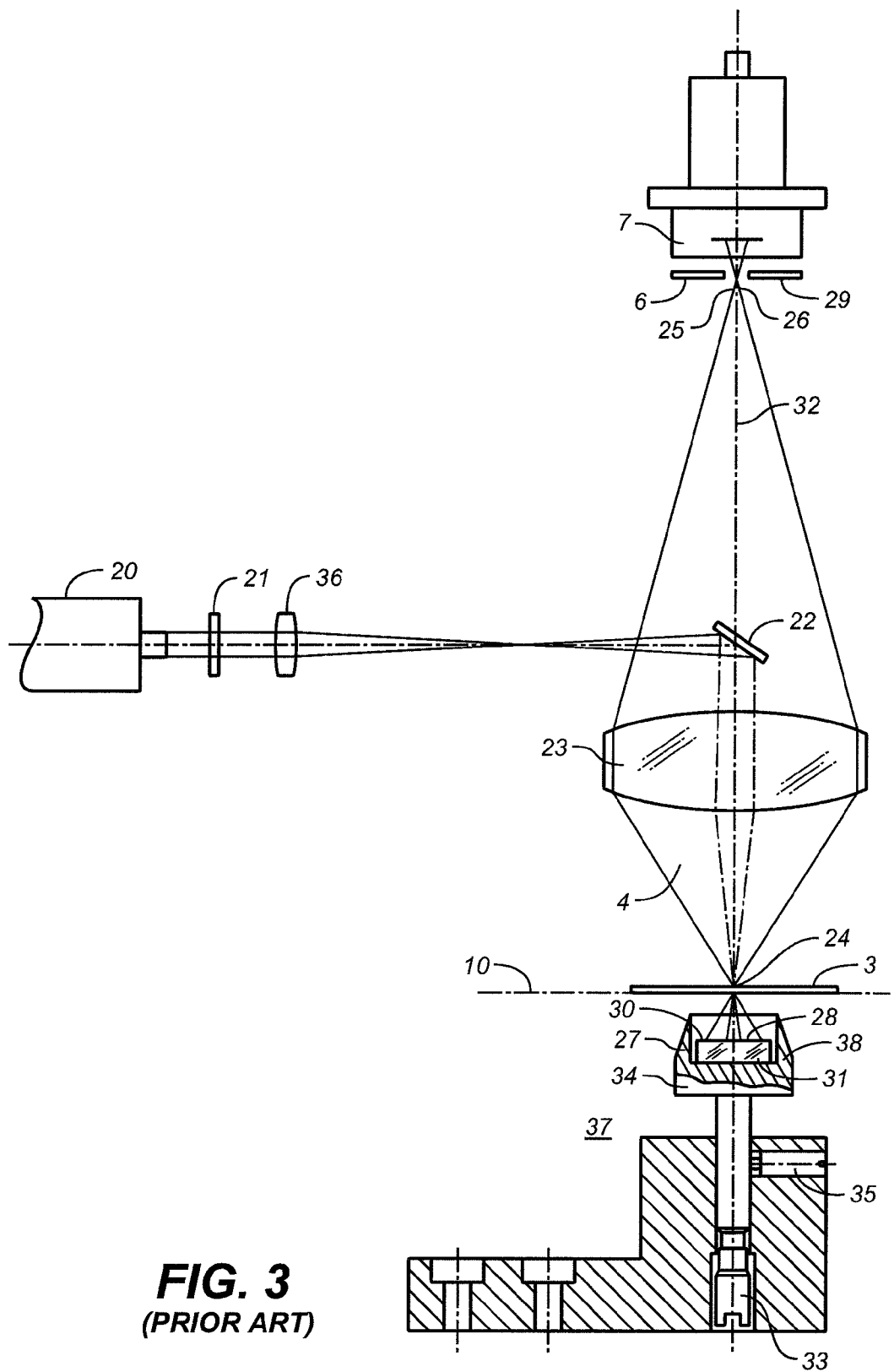
FIG. 3 is a further diagrammatic representation of prior art, but fitted with an assembly as described in the present disclosure.

FIG. 3 shows an assembly of parts of a surface-inspection system. The light emitted by a laser 20 passes through an optical filter 21, for example an attenuator or neutral density filter, to a beam deflector 22, such as a mirror or prism, and thence to a lens 23 which focuses the light to an illuminated spot 24 lying in the focal plane 10. During the inspection procedure the wafer surface 3 subject to inspection lies in the focal plane 10. That portion of the diffused light 4 which is diffused by the wafer surface 3 passes through the collector lens 23 and the collection diaphragm 6 to the photodetector 7. In this confocal system the aperture 25 in the collection diaphragm 6 lies in the image 26 of the illuminated spot 24 and its shape is more or less the same as that of the spot 24. In the calibration phase, a reference medium 27 is placed in position, preferably below the focusing plane 10.

Because the reference medium 27 thus lies beyond the focusing plane 10, the area of a second illuminated spot 28 is greater than the first such spot 24 in the focusing plane 10. Likewise, in the calibration phase, the area 29 thus illuminated in the position of the collection diaphragm 6 is greater than the image 26.

Because the aperture 25 of the collection diaphragm 6 is still in the same size, only a very small proportion of the diffused light from the reference medium 27 now passes through the aperture 25 of the collection diaphragm 6 to the photodetector 7.

An attenuation mechanism for the calibration is formed by means of the optical filter 21 and/or by displacement of the reference medium 27 out of the focusing plane 10.

When the position of the reference medium 27 is moved along the optical axis 32, this alters the size of the illuminated area 29 in the position of the collection diaphragm 6.

Thus, if the size of the aperture 25 in the collection diaphragm 6 is kept constant, this makes it possible to regulate the amount of energy that reaches the photodetector 7.

The typical embodiment shown has an adjustment mechanism 37 which consists of a support 34 adjustable in height by means of an adjustment screw 33, on which the reference medium 27, having surface 30 and volume 31, is placed. The support for the reference medium has a raised rim 38.

In this typical embodiment the height setting can be fixed by means of a clamping screw 35.

Further, it is of course perfectly feasible to integrate at least one refracting element 36, for example a lens, between the light source 20 and the beam deflector 22.

Figure 4:
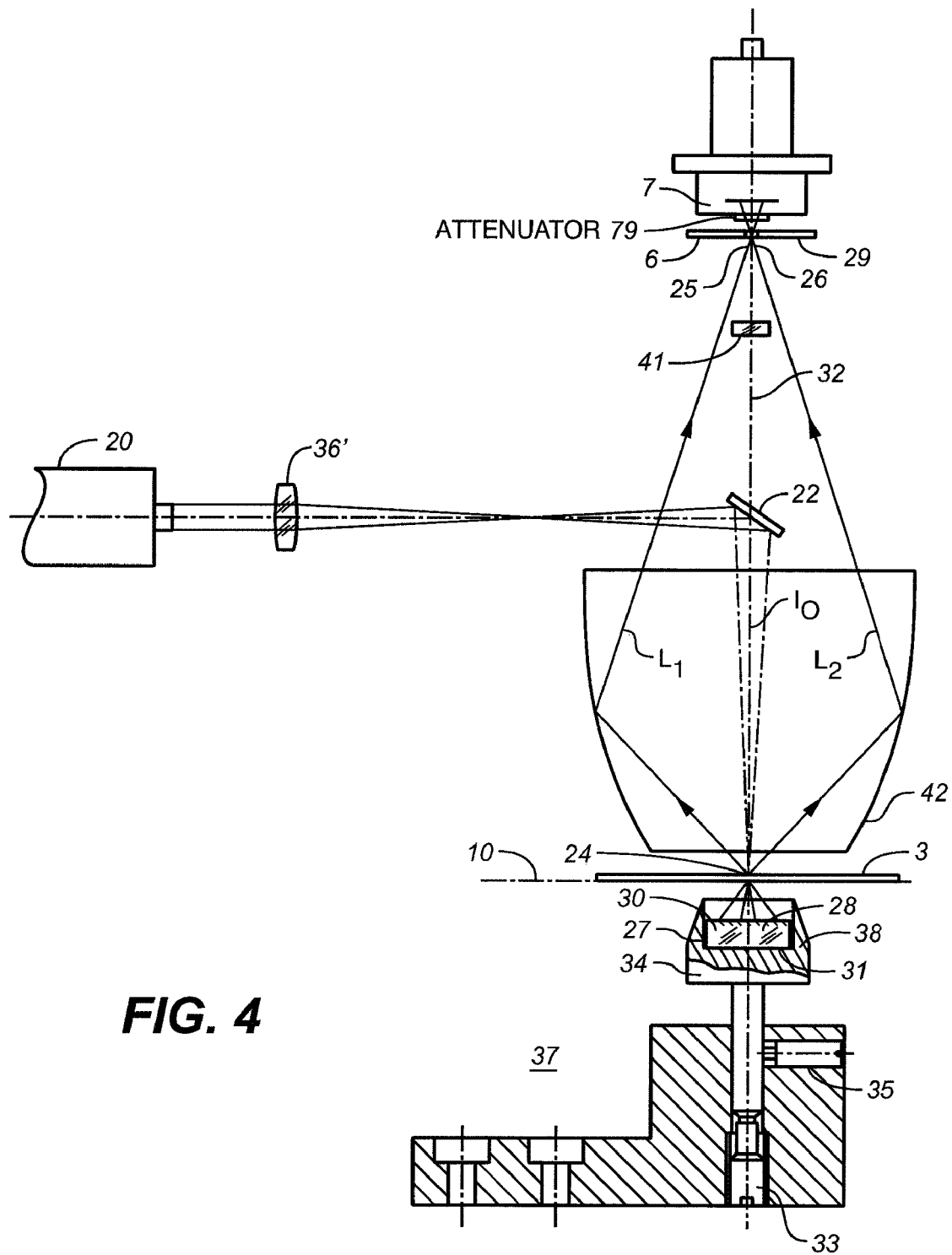
FIG. 4 shows a first embodiment of an assembly as described in the present disclosure.
Figure 6:
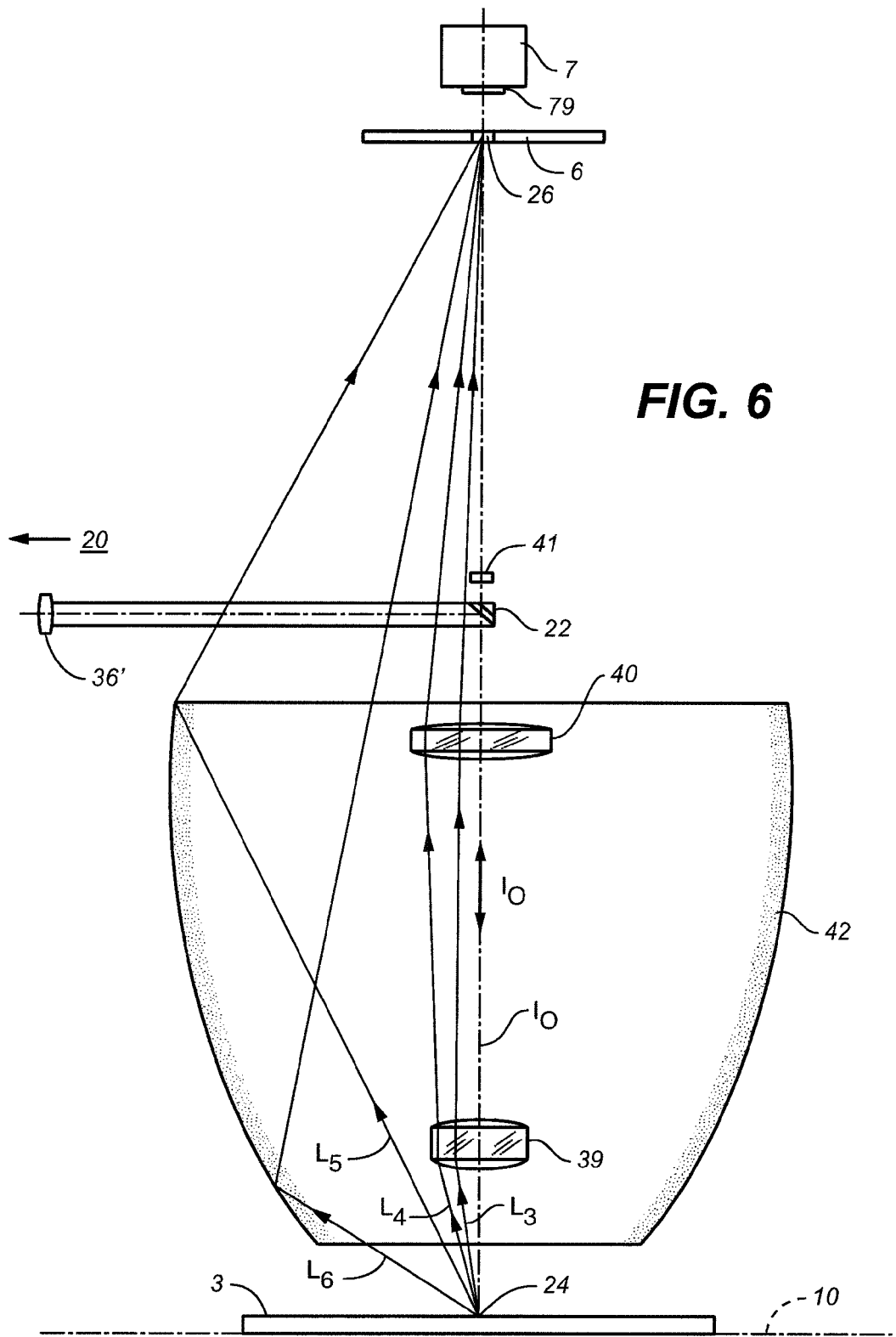
FIG. 6 shows a second embodiment of the assembly as described in the present disclosure.

The lenses, laser light sources, diaphragms, etc., described in FIGS. 3, 4, and 6 can of course be assembled as complete systems, and in practice this is the case. Thus, for example, the light emitted by the light source 20 may be coherent or incoherent, monochromatic or polychromatic, unpolarized or polarized, and elliptical, linear, or circular, and may emanate from one or two lasers of different wavelengths, a mercury-vapor lamp etc. The lens may be a single spherical or cylindrical lens, or a complete lens system. Further, to facilitate adjustments to the optical system, additional mirrors may be placed between the light source 20 and the deflection mirror 22.

For the sake of clarity, the drawings omit these details which may, for example, be necessary for adjustment and/or calibration.

For the purposes of the present disclosure it is also assumed that the process and assembly described in the present disclosure are applied to the prior art, in particular to U.S. Pat. No. 4,314,763 (Steigmeier et al.), wherein the transport system for spiral scanning used to scan the wafer subjected to inspection makes a composite movement consisting of translating and rotation, though the principle as such must be regarded as known.

Moreover, the present disclosure includes a gauge, described below, which is essential to ensure that the light supplied by the light source is perpendicular to the test object's surface and that the light source and the supply of light remain stationary while the test object moves spirally under the light beam during the scanning process, maintaining rotational symmetry.

FIG. 4 shows a first such typical embodiment of a system as described for the invention in the present disclosure. For clarity, this adopts the same reference numbers as those used in FIG. 3 for all features that occur in both figures.

As shown, the light emitted by the source 20 passes through a projection lens 36', via the beam deflector 22, to the illuminated spot 24 on the test object (wafer) 3. In this case, the size and shape of the illuminated spot 24 are determined and adjusted solely by the image produced by the projection lens 36' system. The light $L_O$ directly reflected by the wafer 3 passes along the same path back to the light source, and a dark-field stop 41 helps ensure that the directly reflected near specular light $L_O$ does not reach the photodetector 7.

Any surface inhomogeneities that may be present on the wafer 3 subjected to inspection diffuse the incident light throughout the hemisphere above the illuminated spot 24. An ellipsoidal mirror or mirrored surface 42 is provided to ensure that the maximum amount of the diffused light is transmitted to the photodetector 7; the mirror 42 is fitted rotationally symmetrically about the optical axis above the illuminated spot 24 and below the beam deflector 22.

The internally silvered or aluminized ellipsoidal mirror 42 is shaped as a partial rotation ellipsoid. The beams of diffused light $L_1$ and $L_2$ and all the rotationally symmetrical beams thus collected by the ellipsoidal mirror 42 form the image of the illuminated spot 24 on the aperture 25 of the collection diaphragm 6.

In this system, the collection diaphragm 6 has the task, on the one hand, of preventing unwanted diffused light that may, for example, be produced in the optical components, from reaching the photodetector 7, and, on the other, of allowing the beams of diffused light $L_1$ and $L_2$ from the illuminated spot 24 to pass.

Figure 5A:
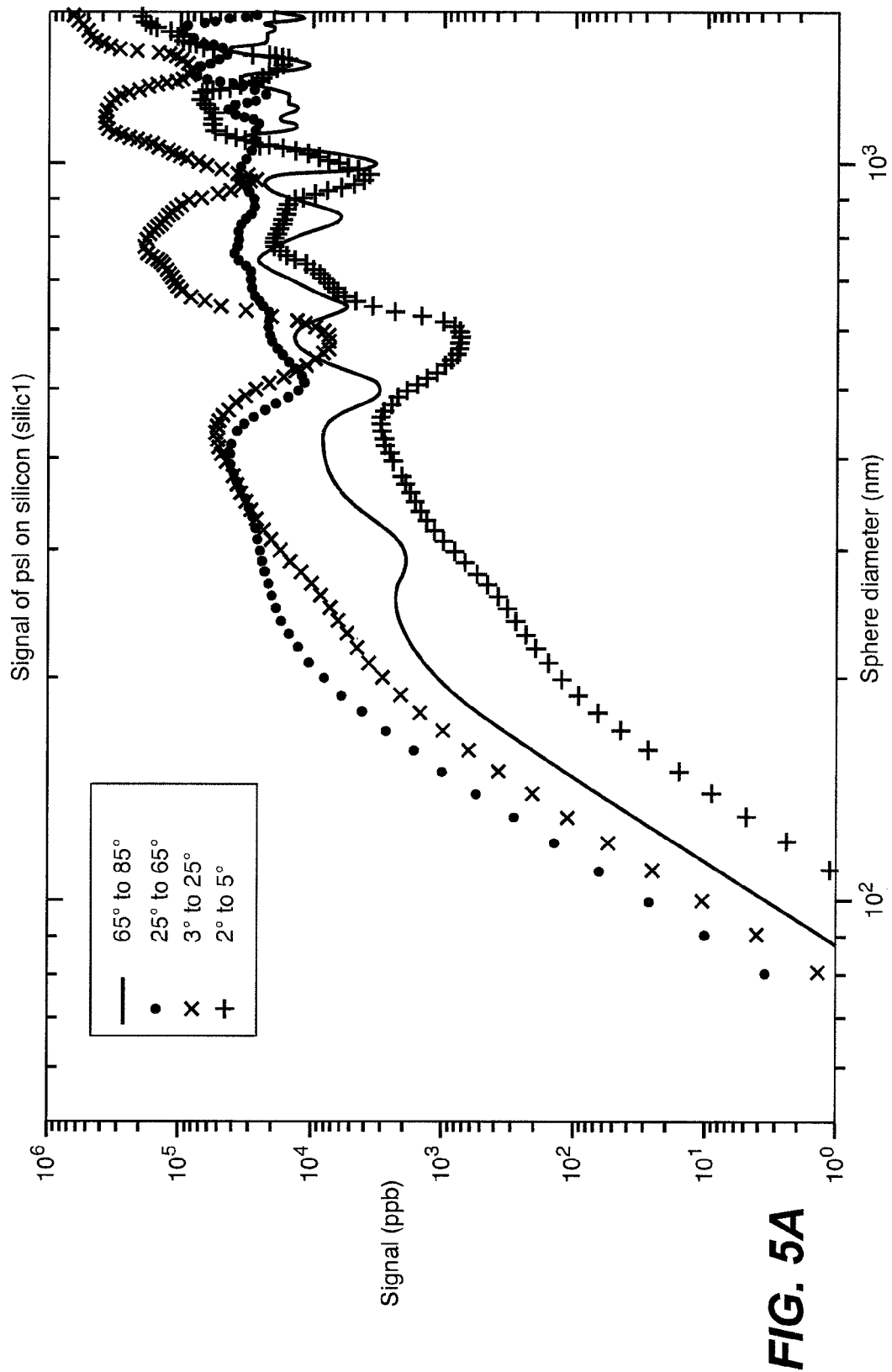
FIG. 5A is a graphical illustration of the scattered light intensity from PSL spheres of different diameters at different angles of collection from the normal direction of the surface.
Figure 5B:
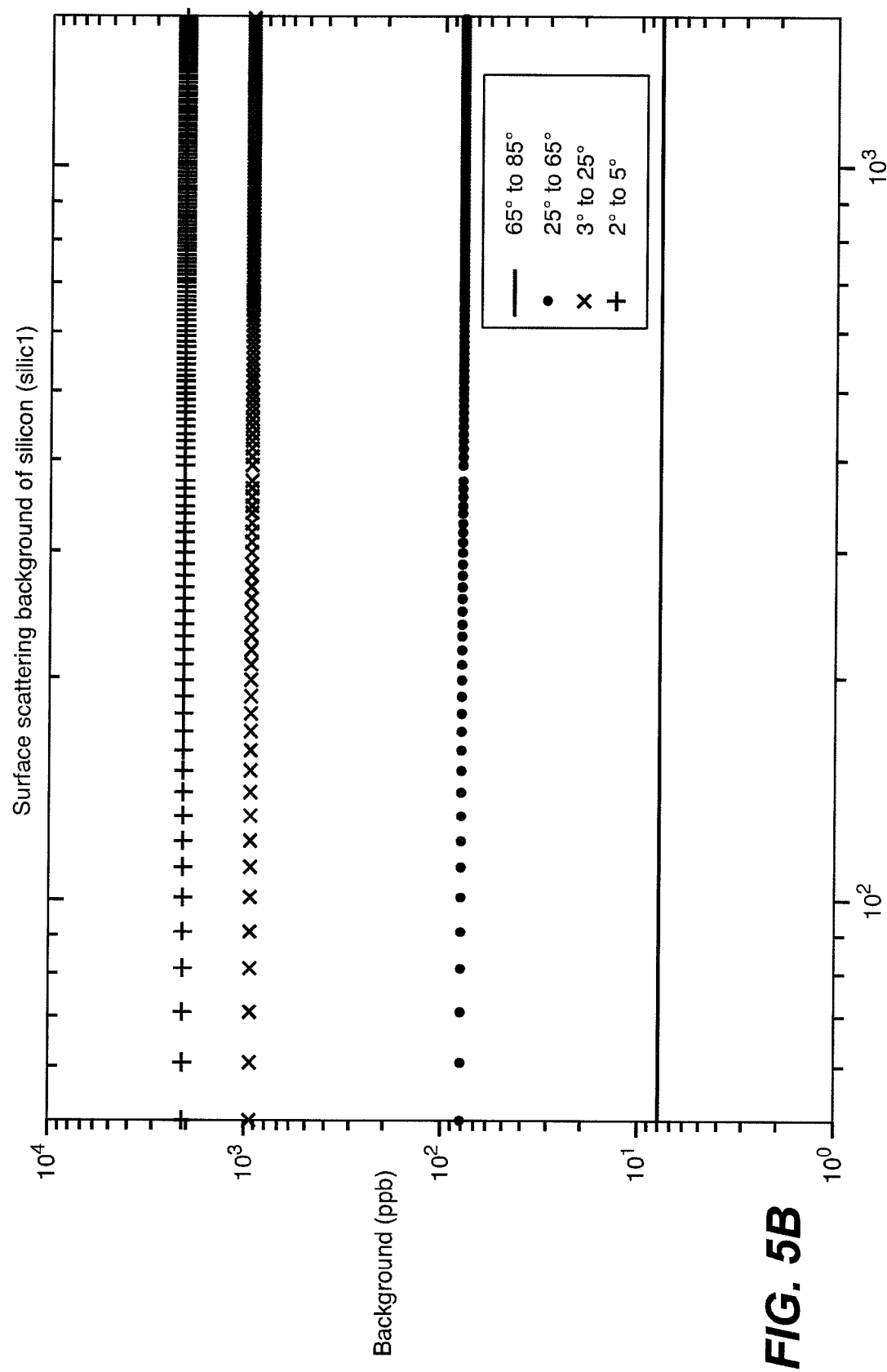
FIG. 5B is a graphical illustration of the surface scattering background intensities of silicon at different angles of collection from the normal direction of the surface.
Figure 5C:
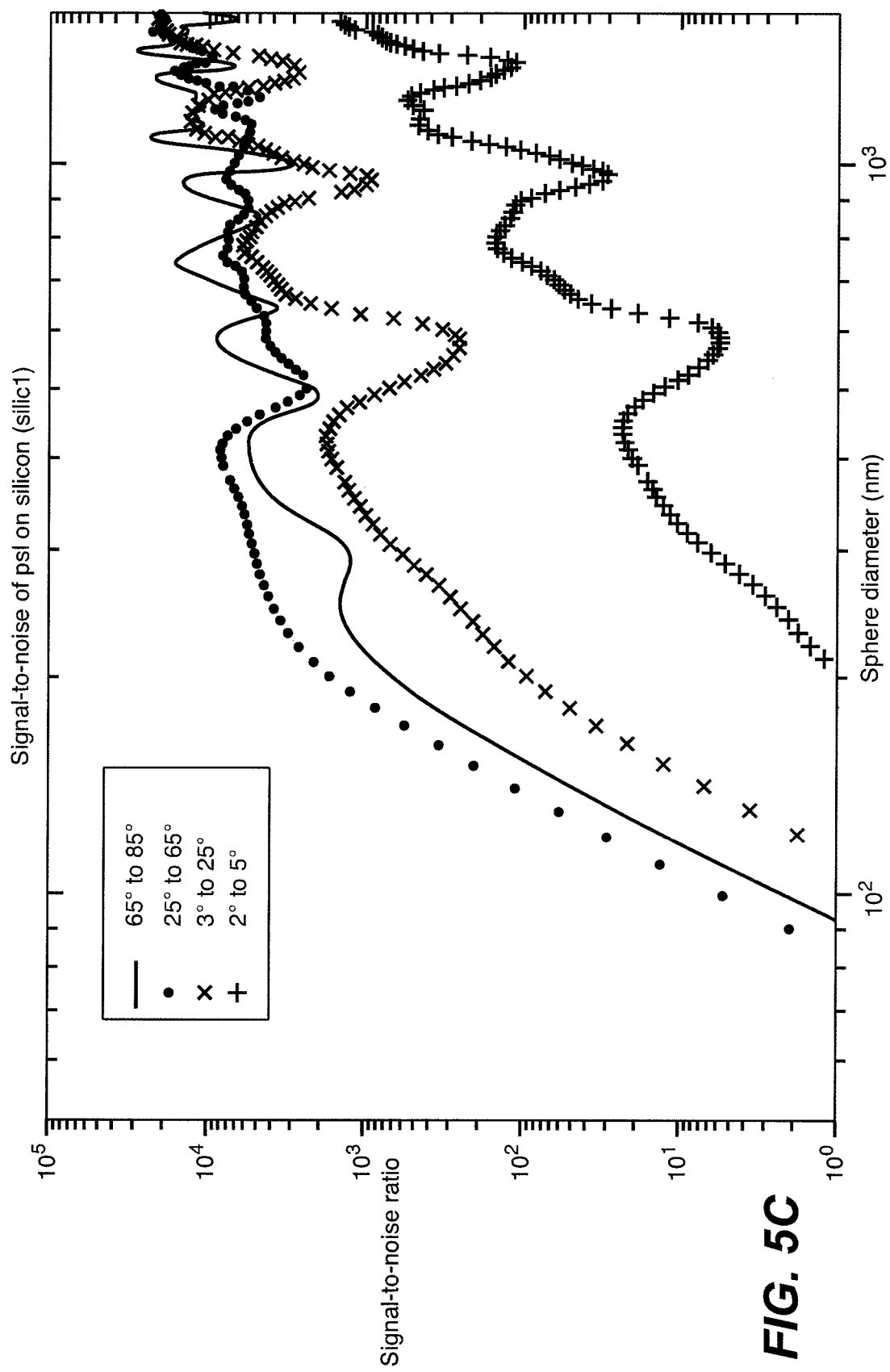
FIG. 5C is a graphical illustration of the signal-to-noise ratio of PSL spheres on silicon at different angles of collection from the normal direction.

The advantages of the optical inspection system of FIG. 4 will now be described in reference to the scattering characteristics of small anomalies illustrated in FIGS. 5A-5C. FIG. 5A is a graphical illustration of the scattering light intensities from PSL spheres of different diameters collected at different angles of collection from the normal direction to the surface. As shown in FIG. 5A, for the same size PSL sphere, the intensity of scattered light at a smaller collection angle to the normal is smaller than that at a larger angle of collection. Sensitivity of detection is the ability to differentiate a signal originating from an anomaly from that originating from background. Therefore, in addition to accounting for the strength of the light signal from the anomaly, the strength of the background signal will also have to be taken into account; this is illustrated in FIG. 5B. As shown in FIG. 5B, it is clear that the scattering background intensity of silicon is much stronger at near specular collection angles in the range of 2 to 5° as compared to that at large collection angles to the normal such as 65 to 85° or 25 to 65°. FIG. 5C is a graphical plot of the signal-to-noise ratio as a function of sphere diameter for the four different ranges of collection angles. From FIG. 5C, it is clear that the signal-to-noise ratio at large collection angles is much better for small particles compared to that at near specular or small collection angles.

The optical system of FIG. 4 includes an ellipsoidal mirror 42 shaped to collect light at large collection angles to the normal direction and avoids collecting light at near specular or small collection angle directions. Thus, from FIG. 5A it is evident that at the same collection angle, the scattering intensity from a large particle is generally higher than that from a smaller particle. It is also further observed that at certain particle size, there will be essentially near zero intensity of scattered light in the range of near specular directions whereas there may still be detectable scattering intensity at larger collection angles. For example, if the scattering intensity from 0 to 5° is avoided altogether, particles smaller than 100 nanometers are still detectable at collection angles of 3 to 25°, 25 to 65° and 65 to 85°. But if the same detector used to detect smaller particles also detects light in the near specular region, detection of light scattered by such small particles will be made difficult by light from the larger particles, and by the surface background as well. At a sphere size of about 100 nanometers, it appears that such smaller spheres are detectable only within the ranges of 3 to 25° and 25 to 65° so that if light is collected only within such ranges, detection of light from such tiny particles will not be made difficult by light from the larger particles and are detectable. However, very large surface scattering (haze) levels will mask the detection of small particles within the collection angles 3 to 25°. The system of FIG. 4 is therefore advantageous for detection of small particles and defects since it collects only light within one or more ranges of the larger collection angles such as 25 to 65°, 65 to 85° and not 2 to 5° or even 3 to 25° from the normal.

FIG. 6 shows the function of two lenses 39 and 40 in connection with the ellipsoidal mirror 42 and the separate rays $L_3$, $L_4$, $L_5$, and $L_6$ that indicate beams of diffused light. The configuration in FIG. 6 may be useful where the number of larger particles or defects on the semiconductor wafer surface is insignificant compared to the small particles or defects and also for very low background surfaces. In such circumstances, it may be advantageous to also collect light in the range of small collection angles 3 to 25° from the normal direction of the surface by means of one or more lenses. However, to include collection in the near specular region (2 to 5°) is undesirable.

The important new features in FIG. 6 are two lenses 39, 40 in the optical path between the beam deflector 22 and the illuminated spot 24, i.e. a first lens 39 and a second lens 40 placed on the optical axis, for the purpose of collecting as much light as possible and focus the light to the same area as the mirror 42. This is exactly the same purpose as that pursued and achieved by the use of an ellipsoidal mirror 42 which is part of a rotation ellipsoid and whose axis of symmetry is parallel to the optical axis, and where the two focal points of the ellipsoid lie, on the one hand, in the illuminated spot 24 and, on the other, in the image 26.

The use of the two lenses 39 and 40 in conjunction with the ellipsoidal mirror 42 increases the collection area.

Two lenses are necessary to prevent the rays from the ellipsoidal mirror striking the focusing unit located on the optical axis and to maximize the area between the beam deflector 22 and the illuminated spot 24. In other words, the use of two lenses enables more light to be collected while retaining the function of focusing the incoming illuminating beam onto spot 24 and the outgoing scattered light onto image 26. The position and focal length of these lenses must be so chosen as to ensure that the focusing unit on the optical axis also forms an image of the light spot on the collection diaphragm 6 in front of the photodetector 7. As described above in connection with FIG. 4, unless it has already been integrated in the beam deflector, the dark-field stop 41 prevents directly reflected near specular laser light and any light diffused by optical components from reaching the photodetector 7.

With the introduction of locally resolved measurements, for example by the use of detector arrays instead of a simple photodetector 7, the signal-to-noise ratio can be further improved, because the effect of haze is equally powerful on all the detectors but the light-point defect (LPD) produces a greater response in some detectors than in others.

To ensure that the photodetector operates in its optimum working range when the substrate subject to inspection produces substantial diffusion, it may be necessary to use attenuators 79 between diaphragm 6 and photodetector 7 to increase the dynamic range of the photodetector.

As already described, the use of combined spherical and cylindrical lenses 36', instead of a simple cylindrical lens 36 in a state-of-the-art assembly, can be useful to adjust the size and shape of the light beam projected to the illuminated spot 24.

Because the brightness of the reflected light that appears in the image 26 is increased by the means described above, angle-resolved measurement also becomes possible, for example by the use of light guides fitted between the collection diaphragm 6 and the photosensor 7, in order to eliminate certain angles of diffusion.

Also to eliminate rays at certain angles of diffusion, the configuration can be further altered by the provision of a second diaphragm 6' (not shown) above or below the collection diaphragm 6.

As noted above, it may be desirable to collect and direct at a detector, light at large collection angles without mixing such collected light with light within small collection angles or near specular reflection for the purpose of detecting tiny particles or defects. Where detection of larger particles and defects is also desired, it may be advantageous to use a second detector to detect light within small collection angles (e.g. 3 to 25 degrees) to the normal in the manner shown in FIG. 7.

Figure 7:
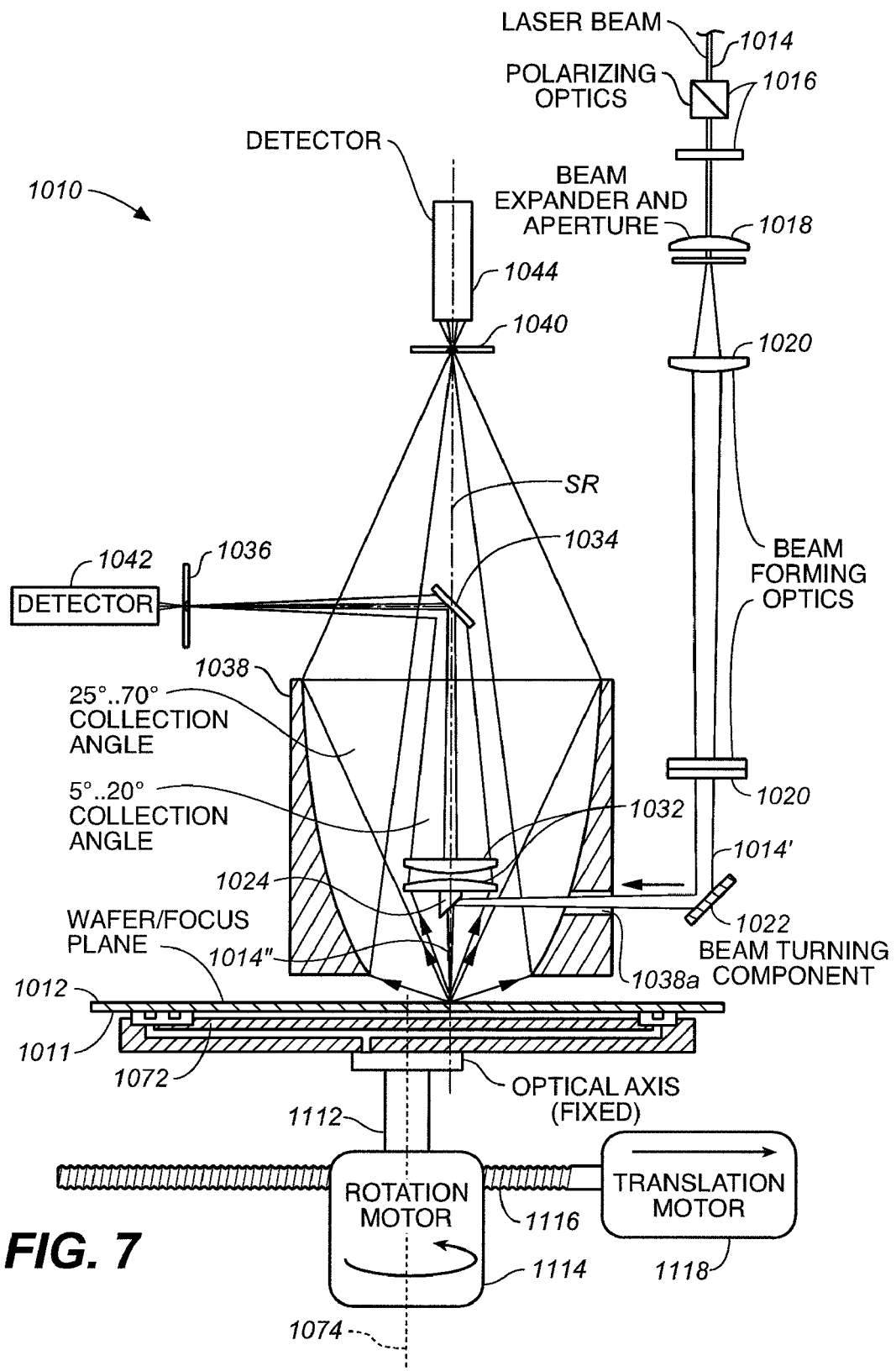
FIG. 7 is a schematic view of a surface inspection system to illustrate the preferred embodiment of the invention.

As shown in FIG. 7, the surface inspection system 1010 may be used for inspecting anomalies on a surface 1012. Surface 1012 is illuminated by a substantially stationary illumination device portion of system 1010 comprising a laser beam from a laser source (not shown). The laser beam 1014 is passed through polarizing optics 1016 of the device portion to cause the laser beam to have the desired polarization state when used to illuminate surface 1012. Laser beam 1014 is then passed through a beam expander and aperture 1018 and beam-forming optics 1020 to expand and focus the beam 1014'. The beam 1014' is then reflected by a beam folding component 1022 and a beam deflector 1024 to direct the beam 1014" towards surface 1012 for illuminating the surface. In the preferred embodiment, beam 1014" is substantially normal or perpendicular to surface 1012, it being understood that this is not required and many of the advantages of the invention described herein are equally applicable where beam 1014" is at an oblique angle to surface 1012.

In the preferred embodiment, beam 1014" is substantially perpendicular or normal to surface 1012 and beam deflector 1024 reflects the specular reflection of the beam from surface 1012 towards component 1022, thereby acting as a shield to prevent the specular reflection from reaching the detectors. The direction of the specular reflection is along line SR normal to surface 1012. In the preferred embodiment where beam 1014" is normal to surface 1012, this line SR coincides with the direction of illuminating beam 1014", where this common reference line or direction is referred to herein as the axis of system 1010. Where beam 1014" is at an oblique angle to surface 1012, the direction of specular reflection SR would not coincide with the incoming direction of beam 1014"; in such instance, the line SR indicating the direction of the surface normal is referred to as the principal axis of the collection portion of system 1010.

Light scattered by small particles are collected by mirror 1038 and directed towards aperture 1040 and detector 1044. Light scattered by large particles are collected by lenses 1032 and directed towards aperture 1036 and detector 1042. Large particles will also, of course, scatter light that is collected and directed to detector 1044, and small particles will also scatter light that is collected and directed to detector 1042 but such light is of relatively low intensity compared to the intensity of scattered light the respective detector is designed to detect.

Figure 8:
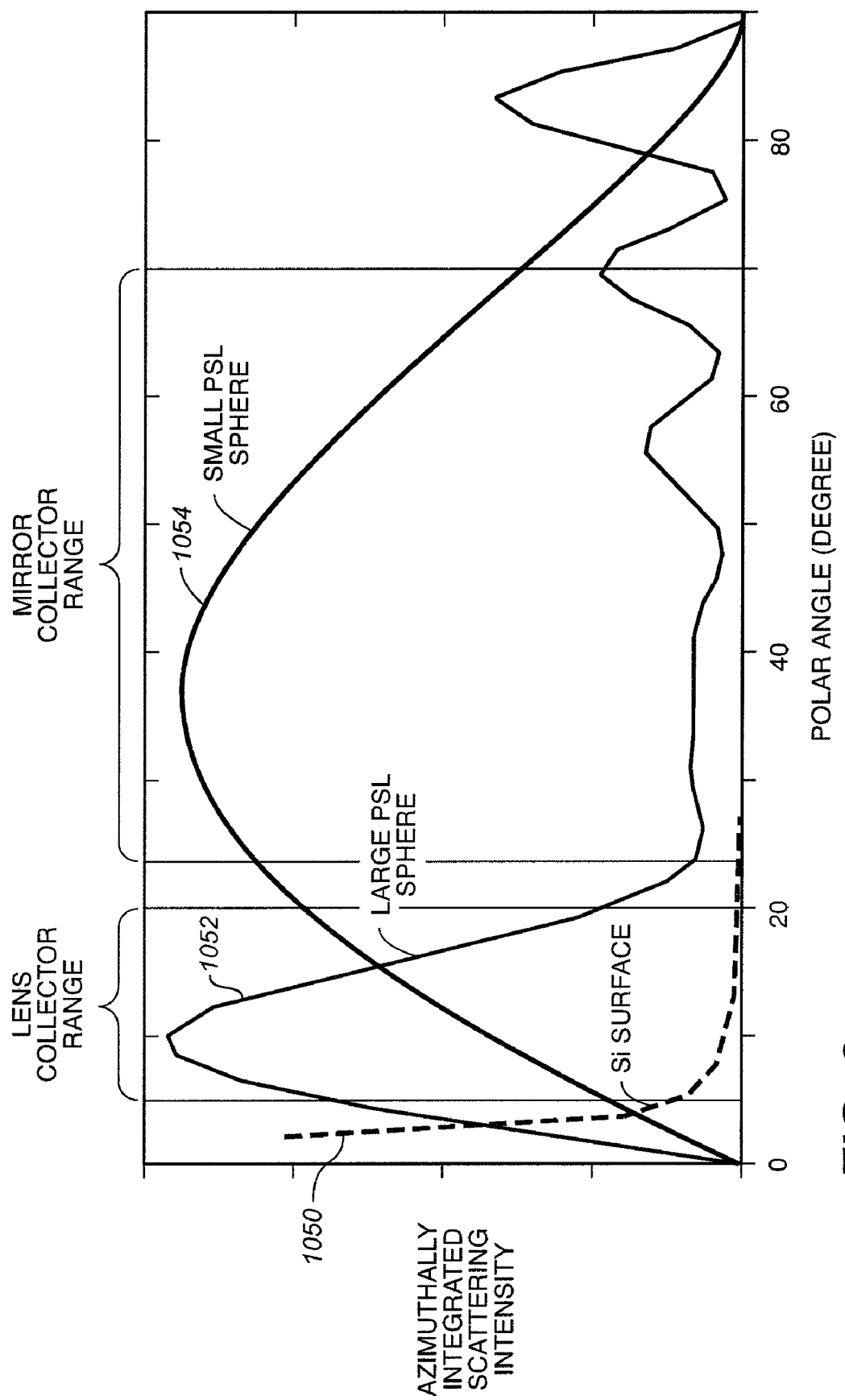
FIG. 8 is a graphical plot of the scattered light intensity from a silicon surface, and from a large and a small PSL sphere placed on the surface to illustrate the invention.

To illustrate the preferred embodiment of the invention, FIG. 8 shows graphical plots of the scattered light intensity (1050) from a silicon surface, that (1054) from a small PSL sphere of the order of 100 nanometers (nm) diameter placed on the surface and that (1052) from a large PSL sphere of the order of 1 micron diameter placed on the surface. In reference to FIG. 7, the polar angle of FIG. 8 indicates the collection angle of the scattered light away from the axis SR of system 1010. Thus, the intensity at a polar angle of zero degrees would indicate the intensity of light reflected or scattered by surface 1012 or the PSL sphere along the axis SR of system 1010 as shown in FIG. 7. As shown by curve 1050, in FIG. 8, the light scattered by the silicon surface falls off rapidly away from the polar angle zero, where specular reflection occurs. The light scattered by the silicon surface away from the specular reflection direction is frequently due to haze; as shown in FIG. 8, light scattering due to haze falls off rapidly with increasing collection angles to the axis of the system. Specular reflection as well as scattered light at collection angles up to about 5° are deflected by deflector 1024 and does not reach any one of the two detectors 1042 or 1044. Light scattered at collection angles within the range of 5-20° from the axis SR of system 1010 are collected by lenses 1032 and deflected by beam deflector 1034 towards an aperture 1036, so that the portion of the beam that passes aperture 1036 is detected by detector 1042. Light scattered at collection angles in the range of about 25 to about 70 degrees are collected by mirror 1038 and focused towards an aperture 1040 so that the light that passes through the aperture is detected by detector 1044.

The angular distribution of light scattered by the small size PSL sphere is shown as the solid line curve 1054 in FIG. 8. As shown in FIG. 8, small particles preferentially scatter at higher angles than a silicon surface. It is also known that small particles scatter at higher angles than larger particles. Whereas the intensity of scattering peaks at around 30-40° for a 100 nanometer PSL sphere, the scattered light intensity typically peaks at much lower scattering angles for large size spheres (about 1 micron diameter and greater). See curve 1052 in FIG. 8. The device portion of system 1010 for collecting and detecting scattered light from anomalies such as large particles is comprised of lenses 1032, a folding mirror 1034, aperture 1036, and detector 1042. Mirror 1038, aperture 1040, and detector 1044 are adapted to detect scattered light from smaller particles, and form the device portion of system 1010 for collecting and detecting scattered light from anomalies such as small particles and defects. Since larger particles typically scatter light at higher intensities compared to smaller particles, the detectors 1042, 1044 can be optimized separately, with detector 1042 optimized for detecting large particles and detector 1044 optimized to detect smaller particles. By using two different detectors for detecting scattered light within two different ranges of collection angles, each detector can be optimized for detecting the respective types of particles and the user is not forced to choose optimization for detecting one type of particle versus the other. Instead both detectors can be optimized to detect their respective types of particles simultaneously.

The meaning of "large" and "small" anomalies discussed above may be phrased in more general terms. In general, an anomaly is small if its dimensions are a fraction of the wavelength of the electromagnetic (laser) radiation used to illuminate the surface inspected. Thus, the plot of FIG. 8 shows the scattering from PSL spheres that are "large" and "small" with respect to visible light wavelengths. If radiation of other wavelengths are used, then the meaning of "large" and "small" anomalies will change according to such wavelengths.

If a single detector or detector arrangement is chosen to detect the light scattering from both large and small particles, a larger dark-field stop must be employed to prevent near angle (near specular) surface scatter from surface 1012 from reaching the detector. This would be necessary in order to maintain the sensitivity of the detector to low intensity scattering from smaller particles. A larger aperture stop would therefore decrease the sensitivity of the system towards light scattering by large particles and also to surface scattering characteristics at near specular angles of collection. This is undesirable. System 1010 of FIG. 7 avoids such undesirable compromise. Since separate detectors 1042, 1044 are now employed, the design of both light collection and detection subsystems need not be constrained so that the range of collection angles for lenses 1032 may be increased to include the near specular collection angles as well. While preferably lenses 1032 collect light that are scattered in a range of 5-20°, such range may be extended to, for example, 3-25°. The larger ranges of collection angles would be useful for particle and defect characterization/classification or surface topography, in some applications.

As shown in FIG. 8, light scattering caused by haze falls off rapidly with increasing collection angles, so that there is negligible light scattering caused by haze that is collected by mirror 1038 and directed towards detector 1044. This further enhances the sensitivity and accuracy of system 1010 for detecting smaller anomalies. In the preferred embodiment, mirror 1038 collects and focuses scattered light in the range of 25-70° from the axis of system 1010 towards aperture 1040 and detector 1044. As indicated above, detectors 1042, 1044 may be optimized separately to have different intensity detection thresholds.

From the above description, it is seen that beam deflector 1024 serves a dual function: to deflect the illuminating beam so as to provide beam 1014" and also acting as a stop to shield detectors 1042, 1044 from specular and near specular (or semi-specular) diffuse reflection. It should also be noted that the illumination portion and the detection device portions of system 1010 are designed so that the illumination beam, in its entire path from the laser source until surface 1012, does not pass through any lens or lens arrangement of the detection system. In the preferred embodiment shown in FIG. 7, this is implemented by placing the beam deflector 1024 between lenses 1032 and surface 1012. An input aperture 1038a in mirror 1038 permits the illuminating laser beam to be passed from beam turning component 1022 to beam deflector 1024 so as to enable beam deflector 1024 to be placed between lenses 1032 and surface 1012. Mirror 1038 is preferably ellipsoidal in shape and also preferably substantially rotationally symmetrical about axis SR of system 1010, so that the same detection result can be obtained repeatedly irrespective of the relative orientation of surface 1012 and of any defects thereon with respect to the illumination and the detection device portions of system 1010. Thus the light detected by detectors 1042, 1044 within the two ranges of collection angles is substantially rotationally symmetrical about the axis of system 1010 upon such light scattering by surface 1012.

Figure 9:
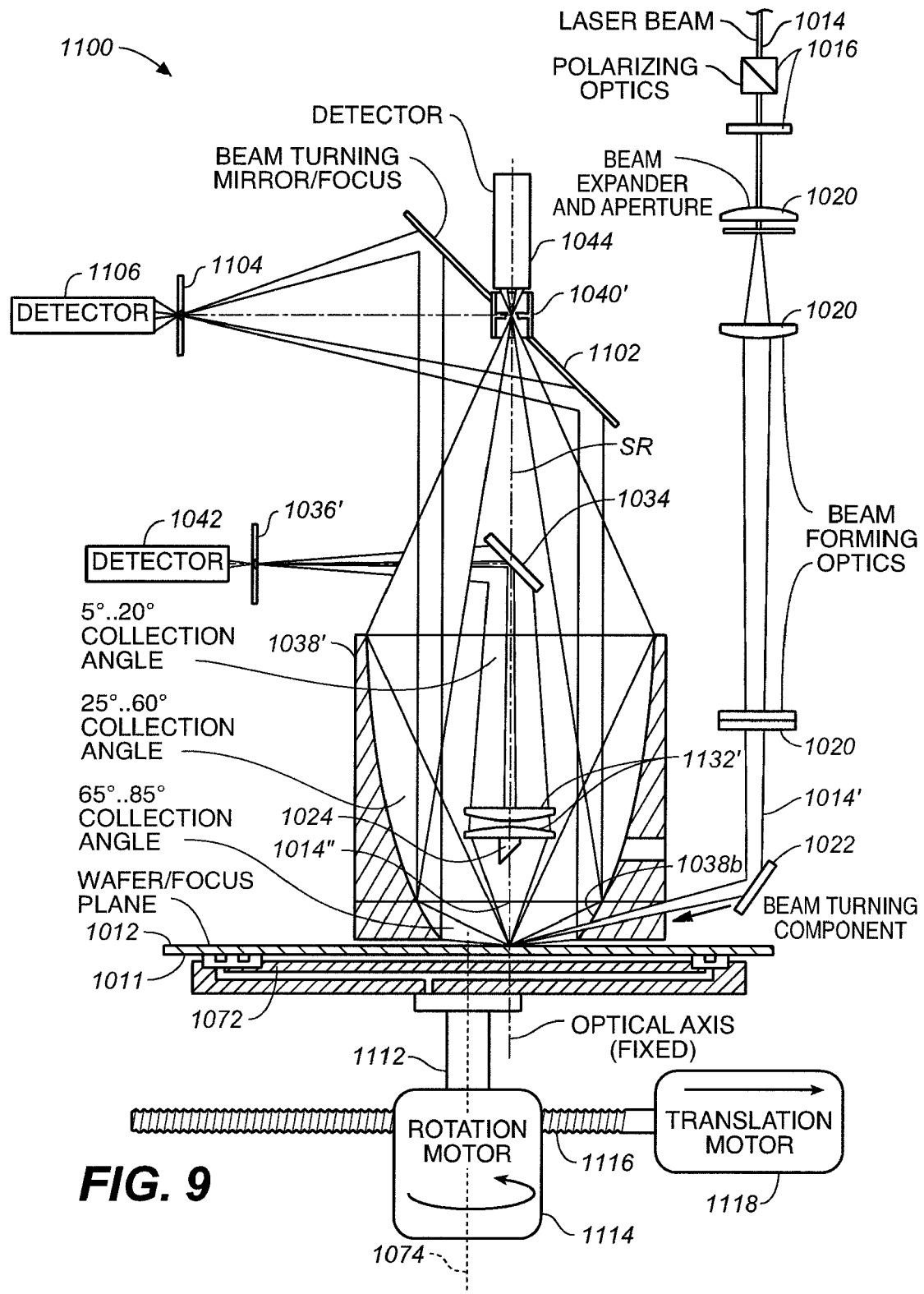
FIG. 9 is a schematic view of a surface inspection system to illustrate an alternative embodiment of the invention.

FIG. 9 is a schematic view of a surface inspection system 1100 to illustrate an alternative embodiment of the invention. The system 1100 is similar to system 1010 of FIG. 6 except that the bottom portion of mirror 1038' has a different curvature than the remaining portion, so that where the remaining portion focuses the light scattered by surface 1012 towards aperture 1040 and detector 1044, portion 1038b has a different curvature so that portion 1038b together with a beam turning component 1102 focus light scattered by surface 1012 towards an aperture 1104 and detector 1106 for detection. Preferably, portion 1038b is paraboloid in shape and it collimates the light scattered from surface 1012, where the collimated light is focused by a curved mirror 1102 towards aperture 1104 and detector 1106. Alternatively, portion 1038b may have a focal point and focuses the scattered light impinging on it towards beam turning component 1102 that reflects such light towards an aperture 1104 and detector 1106 for detection. Portion 1038b and component 1102 preferably collect and focus light in the range of about 65 to 85 degrees from axis SR towards aperture 1104 and detector 1106. The remaining portion of mirror 1038' collects and focuses light in the range of about 25 to 60 degrees from axis SR towards aperture 1040' and detector 1044. The lenses 1032' collects and focuses light in the range of about 5 to 20 degrees (or even 3 to 25 degrees) from axis SR towards aperture 1036' and detector 1042. The use of three sets of light collection optics and detectors to separately detect the scattered light in smaller ranges of angles from axis SR may be advantageous for some applications. Obviously, mirror 1038' may have more than two portions having different curvatures, in order to separately detect the scattered light in more than three smaller ranges of angles from axis SR. Such and other variations are within the scope of the invention.

Rotational and translational movement of surface 1012 is caused in a conventional manner so that beam 1014" scans the surface along a spiral path. Thus, as shown in FIG. 9, the semiconductor wafer 1011 having surface 1012 thereon may be supported by a supporting disk 1072 which is connected to a shaft 1112 having axis 1074 of a rotary motor 1114 which is in turn fixed to a linear translation stage 1116, driven by a translation motor 1118. The rotary and translation motors are controlled in a coordinated manner as known to those skilled in the art to cause simultaneous rotational and translational movement of surface 1012 so that beam 1014" would trace a spiral path on surface 1012. Surface 1012 of FIG. 7 may be caused to travel in the same manner so that beam 1014" scans surface 1012 along a spiral path.

In operation, a light beam such as beam 1014" is directed towards surface 1012 in a specified direction or angle of incidence, causing specular reflection along a direction defining an axis. Rotational and translational movement of the surface is caused so that the beam scans the surface along a spiral path. Light scattered by the surface within the first range of collection angles from the axis is detected by means of a first detector. Light scattered by the surface within the second range of collection angles from the axis is detected by means of a second detector, where the two ranges of collection angles are different. Preferably, the two ranges of collection angles are substantially stationary. Preferably, the axis is substantially normal to the surface.

While the invention has been described above by reference to the preferred embodiment, it will be understood that various changes and modifications may be made without departing from the scope of the invention which is to be defined only by the appended claims. For example, while only one detector has been shown for each of the two detectors 1042, 1044, it will be understood that an array of detectors may be used for each of the two detector locations 1042, 1044. Additional apertures or aperture stops may be employed in the detection and illumination portions of system 1010 than as shown in FIG. 7. The illumination beam and the collector light may also be passed through more or fewer lenses or mirrors of different optical arrangements than as shown in FIG. 7. All such variations are within the scope of the invention. The system described is also advantageous for differentiating between scratches, slip lines, COPs and other topographic features, since one type of such defects may scatter light at a larger angle to the axis compared to another type of such defects.

What is claimed is:

1. An optical system for detecting contaminants and defects of a test surface comprising:
    a device providing a polarized light beam along a path at an oblique angle to the test surface, producing an illuminated spot thereon;
    a first and a second detector;
    a first collector having an optical axis substantially along a line perpendicular to the test surface, said first collector collecting light from the polarized light beam scattered by the illuminated spot of the surface and conveying the collected light to the first detector, causing the first detector to provide a single output in response to the light collected by the first collector; and
    a second collector collecting light from the polarized light beam scattered by the illuminated spot of the surface and conveying the collected light to the second detector, causing the second collector to provide a single output in response to the light collected by the second collector, wherein the first and second collectors collect light scattered by the surface within different ranges of collection angles from the line.

2. An optical system for detecting contaminants and defects of a test surface comprising:
    a device providing a polarized light beam along a path at an oblique angle to the test surface, producing an illuminated spot thereon;
    a first and a second detector;
    a first collector collecting light scattered by the surface and conveying the collected light to the first detector; and
    a second collector collecting light scattered by the surface and conveying the collected light to the second detector, wherein the first and second collectors have an optical axes substantially along a line, said first and second collector collecting light scattered by the surface within different ranges of collection angles that are away from and that do not include a line normal to the test surface,
    said first collector having an optical axis substantially along a line perpendicular to the test surface.

3. The system of claim 2, wherein the first collector collects light scattered from the spot within collection angles of up to 25 degrees from the line.

4. The system of claim 2, wherein the first collector collects light scattered from the spot within collection angles of about 3 to 25 degrees from the line.

5. The system of claim 2, wherein the second collector collects light scattered from the spot within collection angles of about 25 to 70 degrees.

6. The system of claim 2, said system further comprising a third detector, said three detectors located to detect light scattered by the surface within at least a first, second and third range of collection angles from the line, said first range of angles being about 3 to 25 degrees, and said second range being about 25 to 65 degrees, and said third range being about 65 to 85 degrees.

7. The system of claim 2, said system further comprising an instrument causing relative rotational and translational motion between the beam and the surface, so that the beam scans a spiral path on the surface.

8. The optical system of claim 2, wherein the device provides a linearly polarized beam.

9. An optical system for detecting contaminants and defects of a test surface comprising:
    a device providing a polarized light beam along a path at an oblique angle to the test surface, producing an illuminated spot thereon;
    a first and a second detector;
    a first collector collecting light scattered by the surface within a first range of collection angles, said first collector conveying the collected light to the first detector; and
    a second collector collecting light scattered by the surface and conveying the collected light to the second detector, wherein the second collector collects light scattered by the surface within a second range of collection angles that are different from the first range of collection angles, at least one of said first and second ranges of collection angles being away from and do(es) not include any direction normal to the test surface, and wherein said first and second ranges of collection angles do not include any specular reflection direction of the light beam,
    said first collector having an optical axis substantially along a line perpendicular to the test surface.

10. The system of claim 9, wherein the first collector collects light scattered from the spot within collection angles of up to 25 degrees from the line.

11. The system of claim 9, wherein the first collector collects light scattered from the spot within collection angles of about 3 to 25 degrees from the line.

12. The system of claim 9, wherein the second collector collects light scattered from the spot within collection angles of about 25 to 70 degrees.

13. The system of claim 9, said system further comprising a third detector, said three detectors located to detect light scattered by the surface within at least a first, second and third range of collection angles from the line, said first range of angles being about 3 to 25 degrees, and said second range being about 25 to 65 degrees, and said third range being about 65 to 85 degrees.

14. The system of claim 9, said system further comprising an instrument causing relative rotational and translational motion between the beam and the surface, so that the beam scans a spiral path on the surface.

15. The optical system of claim 9, wherein the device provides a linearly polarized beam.

16. An optical method for detecting contaminants and defects of a test surface comprising:
    providing a polarized light beam along a path at an oblique angle to the test surface, producing an illuminated spot thereon;
    collecting light from the polarized light beam scattered by the surface and conveying the collected light to a first detector; and
    collecting light from the polarized light beam scattered by the surface and conveying the collected light to a second detector, wherein the first and second collectors collect light scattered by the surface within different ranges of collection angles that are away from and that do not include a line normal to the test surface, said ranges of collection angles being at different elevations from the test surface,
    wherein said first collector having an optical axis substantially along a line perpendicular to the test surface.

17. The method of claim 16, wherein the collecting and conveying light to the first detector collects light scattered from the spot within collection angles of about 3 to 25 degrees from the line.

18. The method of claim 16, wherein the collecting and conveying light to the second detector collects light scattered from the spot within collection angles of about 25 to 70 degrees.

19. The method of claim 16, said method further comprising causing relative rotational and translational motion between the beam and the surface, so that the beam scans a spiral path on the surface.

20. The optical method of claim 16, wherein the providing provides a linearly polarized beam.

21. The method of claim 16, wherein said method detects small anomalies in the presence of large anomalies on the test surface.

22. The method of claim 16, wherein said method enables differentiation between large and small anomalies.

23. The method of claim 16, wherein said method enables differentiation, characterization and/or classification of anomalies, said anomalies comprising scratches, slip lines, crystal originated particles and particles by comparing light collected by the two detectors.

24. The method of claim 16, wherein said method enables differentiation between scratches, slip lines and crystal originated particles by comparing light collected by the two detectors.

25. The method of claim 16, wherein said method enables differentiation between different topographic features by comparing light collected by the two detectors.

26. An optical method for detecting contaminants and defects of a test surface comprising:
    providing a polarized light beam along a path at an oblique angle to the test surface, producing an illuminated spot thereon;
    collecting light from the polarized light beam scattered by the surface within a first range of collection angles by a first collector, said first collector conveying the collected light to a first detector;
    said first collector providing a single output in response to the light collected by it;
    collecting light from the polarized light beam scattered by the surface and conveying the collected light to a second detector,
    said second collector providing a single output in response to the light collected by it;
    wherein the second collector collects light scattered by the surface within a second range of collection angles that are at different elevations from the first range of collection angles, at least one of said first and second ranges of collection angles being away from and do(es) not include any direction normal to the test surface,
    wherein said first collector having an optical axis substantially along a line perpendicular to the test surface.

27. The method of claim 26, wherein the collecting and conveying light to the first detector collects light scattered from the spot within collection angles of up to 25 degrees from the line.

28. The method of claim 26, wherein the collecting and conveying light to the first detector collects light scattered from the spot within collection angles of about 3 to 25 degrees from the line.

29. The method of claim 26, wherein the collecting and conveying light to the second detector collects light scattered from the spot within collection angles of about 25 to 70 degrees.

30. The method of claim 26, said method further comprising causing relative rotational and translational motion between the beam and the surface, so that the beam scans a spiral path on the surface.

31. The optical method of claim 26, wherein the providing provides a linearly polarized beam.

32. The method of claim 26, wherein said method detects small anomalies in the presence of large anomalies on the test surface.

33. The method of claim 26, wherein said method enables differentiation between large and small anomalies.

34. The method of claim 26, wherein said method enables differentiation, characterization and/or classification of anomalies, said anomalies comprising scratches, slip lines, crystal originated particles and particles.

35. The method of claim 26, wherein said method enables differentiation between scratches, slip lines and crystal originated particles.

36. The method of claim 26, wherein said method enables differentiation between different topographic features.

37. An optical system for detecting anomalies of a sample, comprising:
    optics directing a beam of radiation along a path at an oblique angle onto a surface of the sample;
    at least one detector; and
    an optical device receiving scattered radiation from the sample surface and originating from the beam and focusing the scattered radiation to said detector, causing said at least one detector to provide an output, said device comprising a curved mirrored surface collecting the radiation from the sample surface, said curved mirrored surface having an axis of symmetry substantially coaxial with a line normal to the surface so that directional scattering information in the received scattered radiation relative to the beam is retained.

38. The system of claim 37, said mirrored surface defining an input aperture positioned proximate to the sample surface to receive scattered radiation therethrough from the sample surface.

39. The system of claim 38, said mirrored surface having a paraboloidal portion, the paraboloidal portion reflecting radiation that passes through the input aperture, said device further comprising means for focusing radiation reflected by the mirrored surface to the detector.

40. The system of claim 38, said mirrored surface being an ellipsoidal mirrored surface, the mirrored surface reflecting and focusing radiation that passes through the input aperture.

41. An optical method for detecting anomalies of a sample, comprising:
   directing a beam of radiation along a path at an oblique angle onto a surface of the sample;
   providing a curved mirrored surface to receive scattered radiation from the sample surface and originating from the beam, said curved mirrored surface having an axis of symmetry substantially coaxial with a line normal to the surface so that directional scattering information in the received scattered radiation relative to the beam is retained; and
   detecting the scattered radiation from the mirrored surface by at least one detector to detect anomalies of the sample.

42. The method of claim 41, further comprising focusing radiation reflected by the mirrored surface to a detector.

43. An optical system for detecting anomalies of a sample, comprising:
   optics directing a beam of radiation along a path at an oblique angle onto a surface of the sample;
   at least one detector; and
   an optical device receiving scattered radiation from the sample surface and originating from the beam and focusing the scattered radiation to said detector, causing said at least one detector to provide an output, said device comprising a radiation collector having an axis of symmetry substantially coaxial with a line normal to the surface so that directional scattering information in the received scattered radiation relative to the beam is retained.

44. The system of claim 43, said mirrored surface defining an input aperture positioned proximate to the sample surface to receive scattered radiation therethrough from the sample surface.

45. The system of claim 44, said mirrored surface having a paraboloidal portion, the paraboloidal portion reflecting radiation that passes through the input aperture, said device comprising means for focusing radiation reflected by the mirrored surface to the detector.

46. The system of claim 43, said mirrored surface being an ellipsoidal mirrored surface, the mirrored surface reflecting and focusing radiation that passes through the input aperture.

47. An optical method for detecting anomalies of a sample, comprising:
   directing a beam of radiation along a path at an oblique angle onto a surface of the sample;
   providing a radiation collector to receive scattered radiation from the sample surface and originating from the beam, said collector having an axis of symmetry substantially coaxial with a line normal to the surface so that directional scattering information in the received scattered radiation relative to the beam is retained; and
   detecting the scattered radiation from the collector by at least one detector to detect anomalies of the sample.

48. The method of claim 47, further comprising focusing radiation reflected by the mirrored surface to a detector.

* * * * *